United States Patent
Fournier et al.

(10) Patent No.: US 10,973,985 B2
(45) Date of Patent: Apr. 13, 2021

(54) INJECTION DEVICE HAVING A NEEDLE PROTECTION DEVICE

(71) Applicant: APTAR STELMI SAS, Villepinte (FR)

(72) Inventors: Arnaud Fournier, Paris (FR); Ghislain Fournier, La Rochelle (FR); Mickael Swal, Chauconin Neufmontiers (FR)

(73) Assignee: APTAR STELMI SAS, Villepinte (FR)

( * ) Notice: Subject to any disclaimer, the term of this patent is extended or adjusted under 35 U.S.C. 154(b) by 537 days.

(21) Appl. No.: 14/771,417

(22) PCT Filed: Feb. 25, 2014

(86) PCT No.: PCT/FR2014/050401
§ 371 (c)(1),
(2) Date: Aug. 28, 2015

(87) PCT Pub. No.: WO2014/131985
PCT Pub. Date: Sep. 4, 2014

(65) Prior Publication Data
US 2016/0015905 A1 Jan. 21, 2016

(30) Foreign Application Priority Data
Mar. 1, 2013 (FR) ..................... 13 51842

(51) Int. Cl.
*A61M 5/32* (2006.01)
*A61M 5/50* (2006.01)
(Continued)

(52) U.S. Cl.
CPC ........ *A61M 5/3202* (2013.01); *A61M 5/5086* (2013.01); *A61M 5/343* (2013.01);
(Continued)

(58) Field of Classification Search
CPC .... A61M 2005/312; A61M 2005/3117; A61M 2005/3118; A61M 2005/3107; A61M 5/3202
(Continued)

(56) References Cited

U.S. PATENT DOCUMENTS 4,720,285 A * 1/1988 Pickhard ............. A61M 5/3202
604/192
4,735,311 A * 4/1988 Lowe ................. A61M 5/3202
206/365
(Continued)

FOREIGN PATENT DOCUMENTS

EP 0 328 504 A1 8/1989
EP 1 208 861 A1 5/2002
(Continued)

OTHER PUBLICATIONS

International Preliminary Examination Report on Patentability dated Sep. 3, 2015 from the International Bureau in counterpart International Application No. PCT/FR2014/050401.
(Continued)

*Primary Examiner* — Rebecca E Eisenberg
*Assistant Examiner* — John A Doubrava
(74) *Attorney, Agent, or Firm* — Sughrue Mion, PLLC (57) ABSTRACT

Injection device of fluid product (100) comprising a syringe body (101) and a needle (110) fixed in an axial end projection (102) of the syringe body, said injection device comprising a needle protection device (200), said protection device being, in a storage position, fixed on said injection device, said protection device being removable from said injection device, said protection device comprising an inner body (210) made of substantially supple and/or deformable material and an outer body (220) made of substantially rigid material, said inner body (210), in a storage position, seal-
(Continued)

ingly closing the distribution orifice (111) of said needle (110) and sealingly cooperating with said injection device (100), and said outer body (220) in a storage position, cooperating with said injection device (100) to fix said protection device (200) onto said injection device (100), characterized in that said outer body (220) comprises a fixing part (228) fixed to said injection device (100) and a protection part (229) fixed to said inner body (210), said protection part (229) being connected to said fixing part (228) by at least one breakable material bridge (227), said at least one breakable material bridge (227) being broken to remove said protection part (229) and said inner body (210) from said injection device (100).

12 Claims, 7 Drawing Sheets (51) Int. Cl.
  *A61M 5/31* (2006.01)
  *A61M 5/34* (2006.01)
(52) U.S. Cl.
  CPC ............... *A61M 2005/312* (2013.01); *A61M 2005/3107* (2013.01)
(58) Field of Classification Search
  USPC ........................................................ 604/192
  See application file for complete search history.

(56) References Cited

U.S. PATENT DOCUMENTS

| | | | |
|---|---|---|---|
| 4,950,249 A | 8/1990 | Jagger et al. | |
| 4,986,818 A | 1/1991 | Imbert et al. | |
| 5,746,733 A | 5/1998 | Capaccio et al. | |
| 6,186,980 B1 | 2/2001 | Brunel | |
| 7,331,941 B2 * | 2/2008 | Vetter | A61M 5/001 604/163 |
| 2002/0062108 A1 * | 5/2002 | Courteix | A61M 5/3202 604/198 |
| 2003/0236501 A1 | 12/2003 | Donnan et al. | |
| 2005/0027259 A1 * | 2/2005 | Vetter | A61M 5/3202 604/192 |
| 2005/0038391 A1 * | 2/2005 | Wittland | A61M 5/3202 604/192 |
| 2012/0330243 A1 * | 12/2012 | Liversidge | A61M 5/3213 604/198 |
| 2013/0030365 A1 * | 1/2013 | Liversidge | A61M 5/3202 604/111 |

FOREIGN PATENT DOCUMENTS

| | | |
|---|---|---|
| EP | 1 466 638 A2 | 10/2004 |
| EP | 1 759 729 A1 | 3/2007 |
| EP | 1 795 220 A1 | 6/2007 |
| FR | 1 272 330 A | 9/1961 |
| FR | 2 777 787 A1 | 10/1999 |
| FR | 2 803 530 A1 | 7/2001 |
| WO | 86/003126 A1 | 6/1986 |
| WO | 01/072362 A1 | 10/2001 |
| WO | 02/011799 A1 | 2/2002 |

OTHER PUBLICATIONS

International Search Report for PCT/FR2014/050401 dated Jul. 1, 2014 [PCT/ISA/210]
International Preliminary Examination Report for PCT/FR2014/050401 dated Jul. 1, 2014 [PCT/IPEA/409].

* cited by examiner

INJECTION DEVICE HAVING A NEEDLE PROTECTION DEVICE

CROSS REFERENCE TO RELATED APPLICATIONS

This application is a National Stage of International Application No. PCT/FR2014/050401 filed Feb. 25, 2014, claiming priority based on French Patent Application No. 13 51842 filed Mar. 1, 2013, the contents of all of which are incorporated herein by reference in their entirety.

The present invention relates to an injection device comprising a needle protection device.

Needle protection devices, also called needle protectors, are well known. There are different types of them, including rigid needle protectors, comprising an inner body made of supple material and an outer body made of rigid material. The inner body ensures sealing both with the orifice of the needle and with the injection device, in general the syringe body, whereas the outer body serves to fix and maintain the needle protector on the injection device until it is used. Documents EP 1 208 861 and FR 2 777 787 in particular describe needle protection devices of this type. Documents U.S. Pat. No. 6,186,980, WO 01/72362, WO 86/03126, EP 0 328 504, FR 1 272 330 and U.S. Pat. No. 4,986,818 describe other devices of the prior art.

These devices can have disadvantages. Therefore, it is not possible to prevent unwanted or accidental withdrawal of the needle protector before use of the associated injection device, which would involve risk of contamination of the needle. Also, due in particular to manufacturing tolerances, in particular glass syringes, it can be difficult in some cases to guarantee sealing in a storage position between the deformable inner body of the needle protector and the injection device, in this case the glass syringe body. Also, manufacture and assembly of the needle protector, and in particular of the outer body on the inner body, can be complex and therefore costly. Also, if the needle protector is effective in storage position, it does not prevent any risk of injury with the needle after use of the injection device.

The aim of the present invention is to provide an injection device which does not replicate the above disadvantages.

The aim of the present invention is therefore to provide a needle protection device of an injection device ensuring sealing before use.

Another aim of the present invention is to provide such a needle protection device which indicates to the user whether the sealing has been broken before use.

Another aim of the present invention is to provide such a needle protection device which is simple and easy to manufacture and assemble, and reliable in use.

The aim of the present invention therefore is an injection device of fluid product comprising a syringe body and a needle fixed in an axial end projection of the syringe body, said injection device comprising a needle protection device, said protection device being, in a storage position, fixed on said injection device, said protection device being removable from said injection device, said protection device comprising an inner body made of substantially supple or deformable material and an outer body made of substantially rigid material, said inner body, in a storage position, sealingly closing the distribution orifice of said needle and sealingly cooperating with said injection device, and said outer body, in a storage position, cooperating with said injection device to fix said protection device on said injection device, said outer body comprising a fixing part fixed to said injection device and a protection part fixed to said inner body, said protection part being connected to said fixing part by at least one breakable material bridge, said at least one breakable material bridge being broken to remove said protection part and said inner body from said injection device.

Advantageously, the force necessary to withdraw said fixing part from said injection device is greater than the force necessary to break said at least one breakable material bridge.

Advantageously, said axial end projection is defined between an axial end surface of the syringe body and a radial projection, said fixing part of the outer body being clipped on to said axial end projection.

According to an advantageous variant, a tongue is interposed between said fixing part and said protection part, said tongue being connected to said fixing part by at least one breakable material bridge and being connected to said protection part by at least one breakable material bridge.

According to another advantageous variant, said protection part of the outer body comprises at least one manual deformation area, the rupture of the material bridge(s) is achieved by clamping of said at least one manual deformation area.

Advantageously, two diametrically opposite manual deformation areas are provided, each of said manual deformation areas being connected to at least one material bridge which breaks when said corresponding manual deformation area is deformed manually.

Advantageously, said inner body comprises a radial projection and said outer body comprises a radial shoulder and a radial end edge defining an upper axial opening, said inner body being inserted into said outer body through said upper axial opening, with said radial projection stopped on said radial shoulder, said axial end edge of said outer body being folded back on said inner body to fix said inner body in said outer body.

Advantageously, said axial end edge of said outer body is folded back on said inner body before assembly of said needle protection device on said injection device.

Advantageously, the device comprises a protection system against accidental pricks.

Advantageously, said protection system comprises protective flaps forming an integral part of said outer body, said protective flaps being movable between a covering position, in which they cover the needle and an open position, in which the needle is uncovered, said protection system further comprising a control ring sliding on said outer body for, before injection, moving said protective flaps from their covering position towards their open position, then after injection, from their open position towards their covering position.

Advantageously, said inner body is made of rubber.

These characteristics and advantages and others of the present invention will emerge more clearly from the following detailed description, given in reference to the appended drawings given by way of non-limiting examples, in which.

The present invention will be described in reference to several variant embodiments of a needle protection device for an injection device. It is nevertheless understood that the present invention is not limited by the embodiments illustrated in the drawings.

Figure 1:
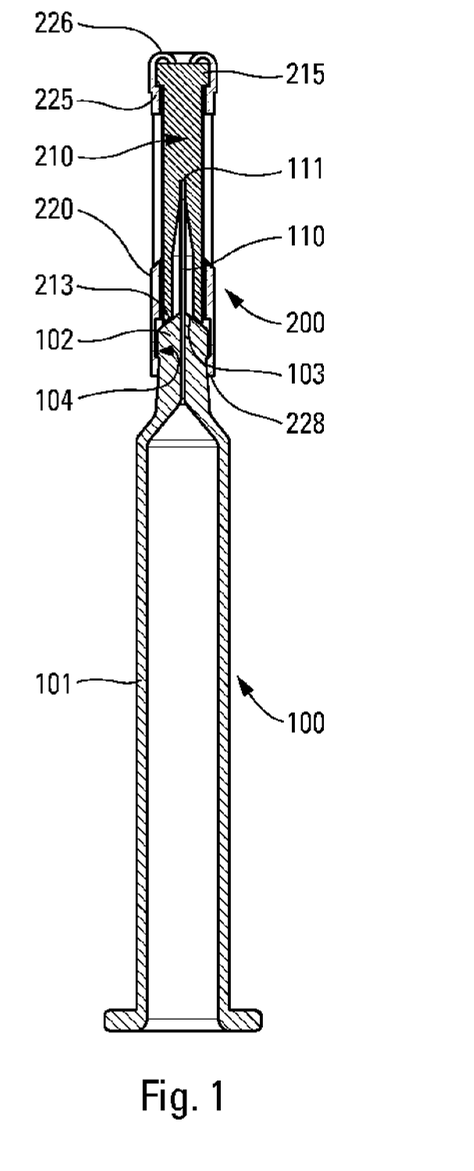
FIGS. 1 and 2 are schematic views in transversal section of a needle protection device according to a first advantageous variant embodiment, respectively in a storage position on an injection device and in withdrawn position.
Figure 2:
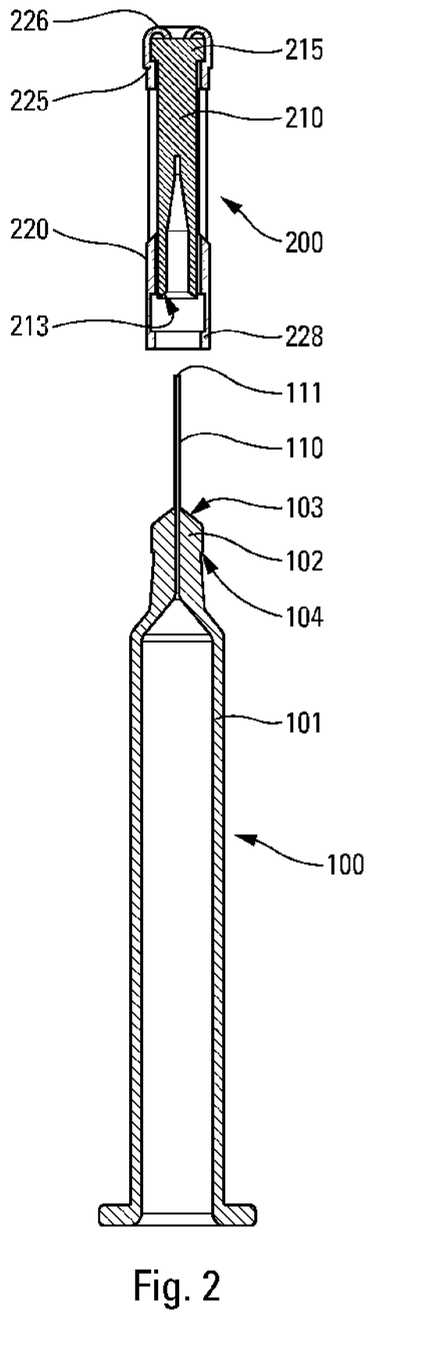

In reference to FIGS. 1 and 2, these illustrate an injection device which in this example is a syringe 100 provided with a syringe body 101 and a needle 110 comprising a distribution orifice 111. The axial end part of the syringe body where is fixed the needle 110 comprises an axial end projection 102, generally called bowl of the syringe, defined between the axial end surface 103 of the syringe body and a radial projection 104 provided to receive and fix a needle protection device 200, to be described hereinbelow. The needle typically has a length of 12.7 mm (½ inch), 15.9 mm (⅝ inch) or 25.4 mm (1 inch). Other dimensions are also possible.

A needle protection device 200 is provided to protect and maintain sealed said needle until the injection device is used. The needle protection device 200 is fixed on said injection device 100 in a storage position, and it is removable, that is, it can be removed from said injection device when said injection device is being used. The needle protection device 200 comprises an inner body 210 and an outer body 220.

The inner body 210 is made of substantially supple or deformable material, such as for example polyisoprene, styrene-butadiene (SBR), a thermoplastic elastomer (TPE) or any other elastomer. Other materials are also possible. The inner body 210 comprises a full part which, in a storage position of the needle protection device, receives the distribution orifice 111 of the needle 110. The axial end of the needle 110 is therefore embedded in said inner body 210 in said storage position. The inner body 210 also comprises a radial projection 215 formed at the distal axial end of said inner body relative to said injection device. On the other side, at the other axial end, the inner body 210 forms a hollow sleeve and comprises a proximal axial end edge 213 relative to the injection device whereof the form is complementary to the axial end surface 103 of the bowl of the syringe 102.

The outer body 220 is made, preferably single piece, of substantially rigid material, such as for example polypropylene (PP), polystyrene (PS), polyoxymethylene (POM) or polybutylene terephthalate (PBT). Other materials are also possible. The outer body 220 comprises a fixing part 228 which is adapted to cooperate with the syringe body 101, in particular with the bowl of the syringe 102, and more particularly with the radial shoulder 104, to fix, in particular by clipping, said needle protection device 200 onto said injection device 100. The outer body 220 comprises on the other side, namely on the distal side relative to the injection device, a radial shoulder 225 and an axial end edge 226 which defines an upper axial opening. Said axial end edge can be folded back inwardly, as will be explained later.

The needle protection device 200 is advantageously made by molding inner body 210 and outer body 220, then assembly of the inner body in the outer body. Preferably, the inner body is inserted into the outer body via the upper opening until the radial projection 215 of the inner body 210 comes to bear on the radial shoulder 225 of the outer body 220. The axial end edge 226 of the outer body 220 is then folded back for fixedly holding the inner body 210 in the outer body 220. This folding back is preferably done before assembly of the needle protection device 200 on the injection device 100, but it could also be done after this assembly. Folding back of the axial end edge 226 is preferably done under heat, typically between 100° C. and 200° C. as a function of the material of said outer body.

In the storage position, sealing with the needle 110 is achieved by embedding the distribution orifice 111 of the needle 110 in the supple or deformable material of the inner body 210. The sealing with the injection device is advantageously achieved by contact between the axial end edge 213 of the inner body and the axial end surface 103 of the bowl of the syringe 102. This sealing is reinforced by compression of the inner body 210 on the axial end surface 103 of the bowl of the syringe 102, compression generated in particular by the position of the radial shoulder 225 and the length of the inner body 210 and/or pressure of the outer body 220 on the inner body 210 at the level of the folding back 226.

The sealing in storage position with the injection device, in particular the syringe body, is advantageously effected only by contact of said proximal axial end edge 213 of the inner body 210 with the axial end surface 103 of the bowl of the syringe 102. In this case, said inner body is preferably made of rubber, which has much better properties relative for example to TPE (thermoplastic elastomer). In this way, rubber in particular has the following properties: a hardness greater than 60 Shore A, an elasticity greater than 10 MPa, a compression set less than 25%, a density greater than 1, in particular greater than 1.3. Also, rubber has no or only very few dimensional variations in case of treatment at high temperatures, for example around 120° C. for the steam sterilisation. By comparison, on this occasion the TPE can have withdrawals, that is, dimensional decreases of up to 3%. In the case of an inner body of a needle protection device, such withdrawal can signify loss of sealing in storage position.

Figure 3:
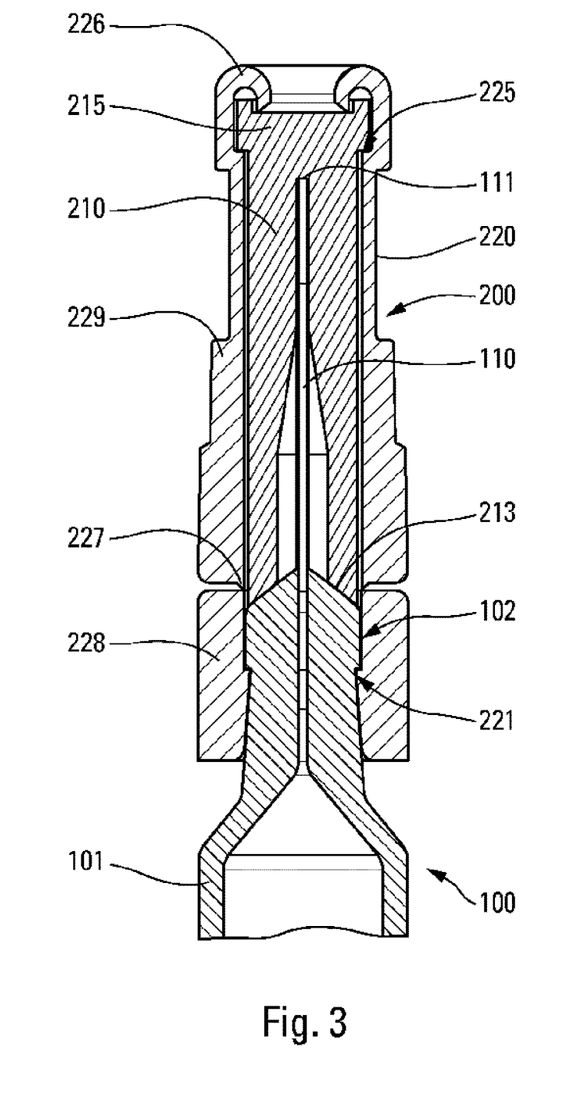
FIGS. 3 to 5 are schematic views in transversal section of three other advantageous variant embodiments, in storage position.
Figure 4:
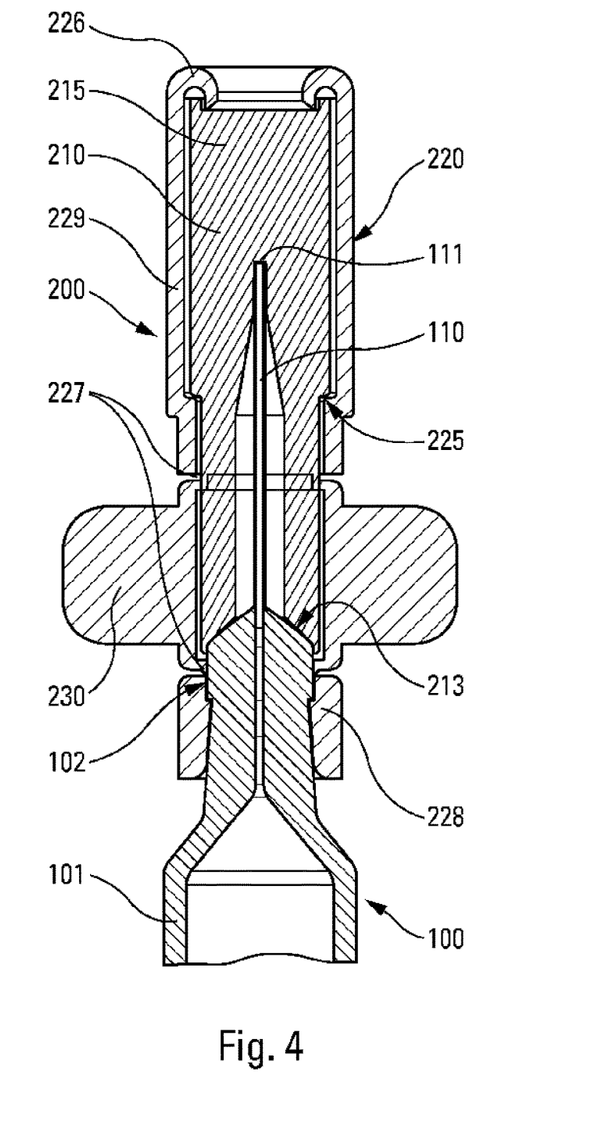
Figure 5:
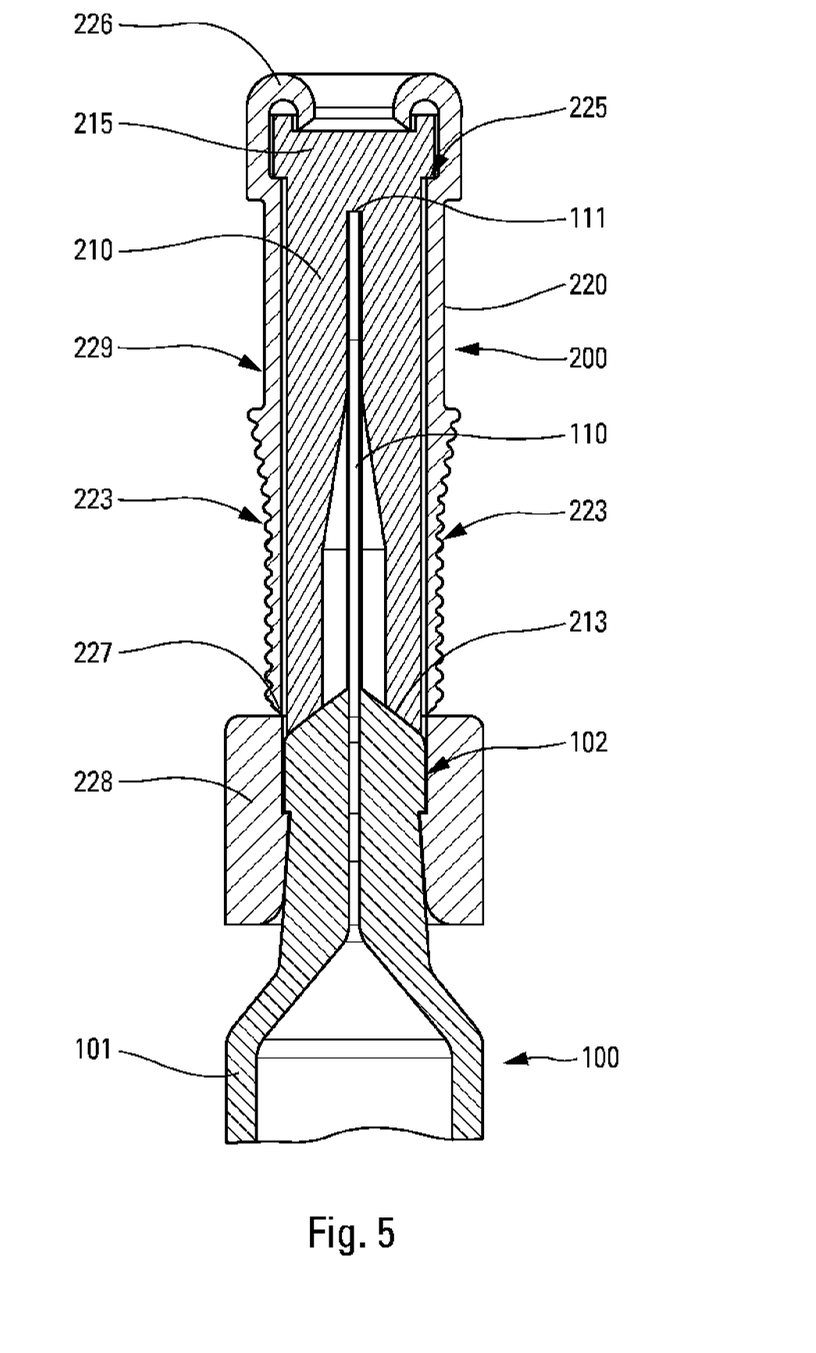
Figure 6:
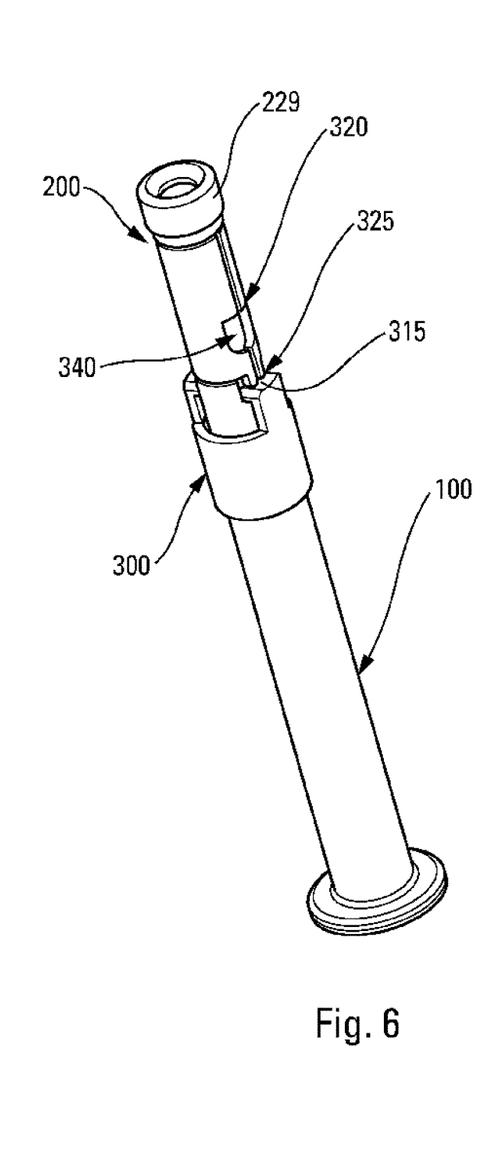
FIG. 6 is a schematic perspective view of yet another variant embodiment, in storage position.
Figure 7:
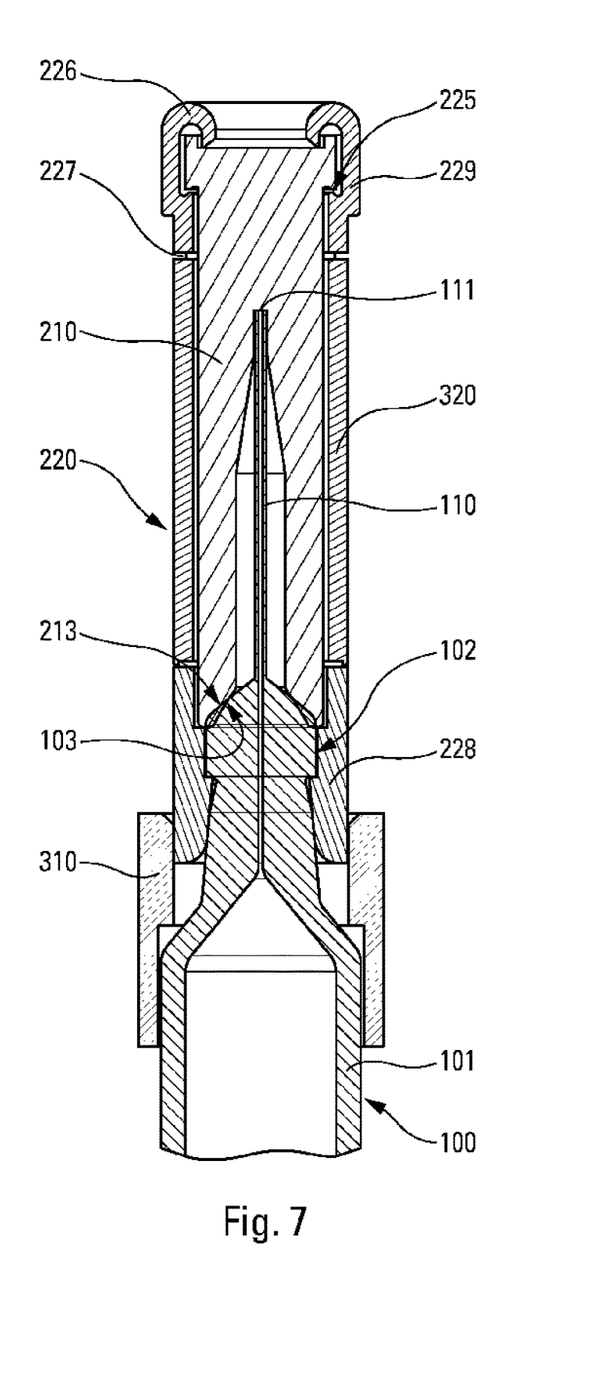
FIG. 7 is a schematic view in transversal section of the device of FIG. 6.
Figure 8:
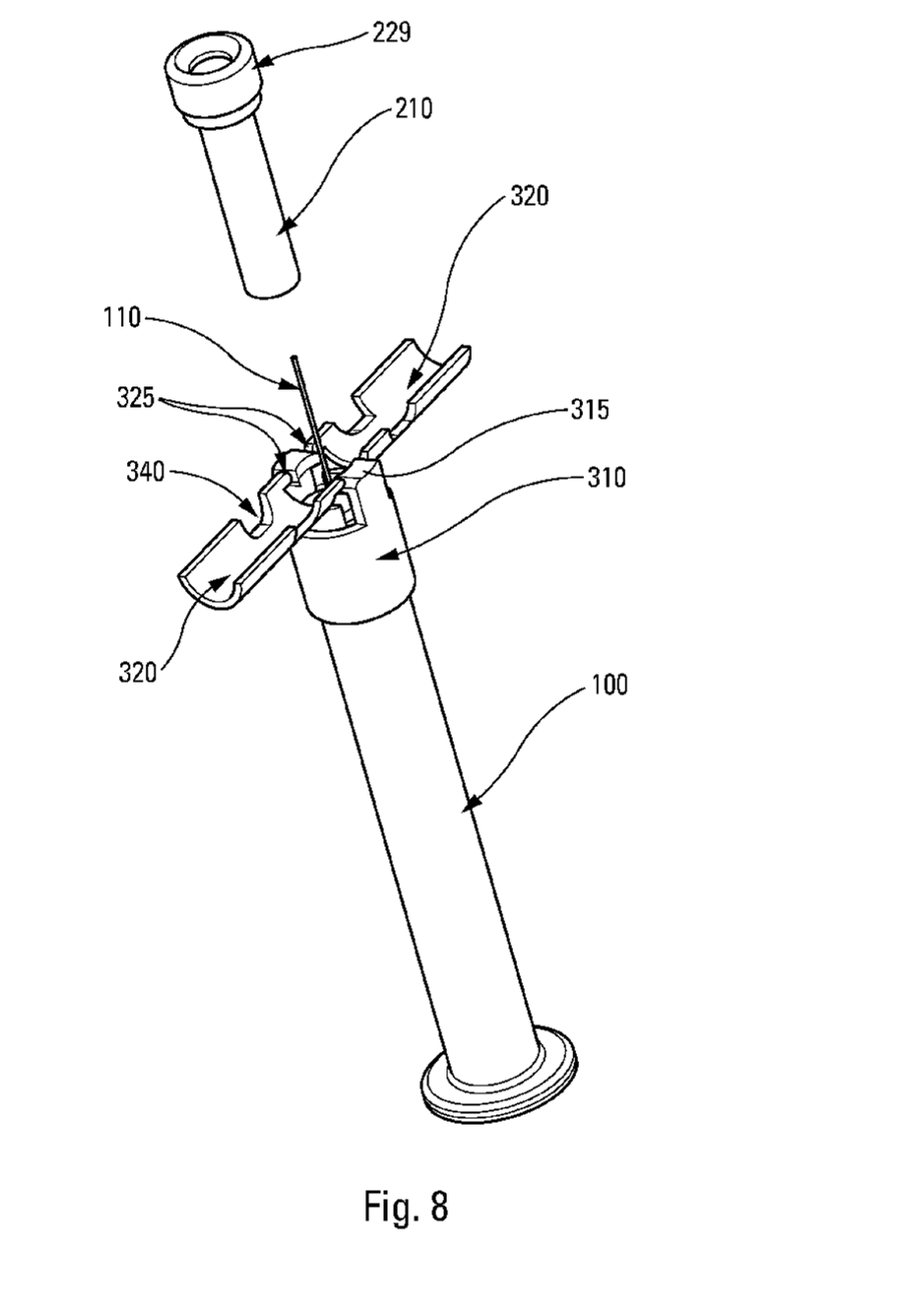
FIG. 8 is a view similar to that of FIG. 6, in use position of the injection device.
Figure 9:
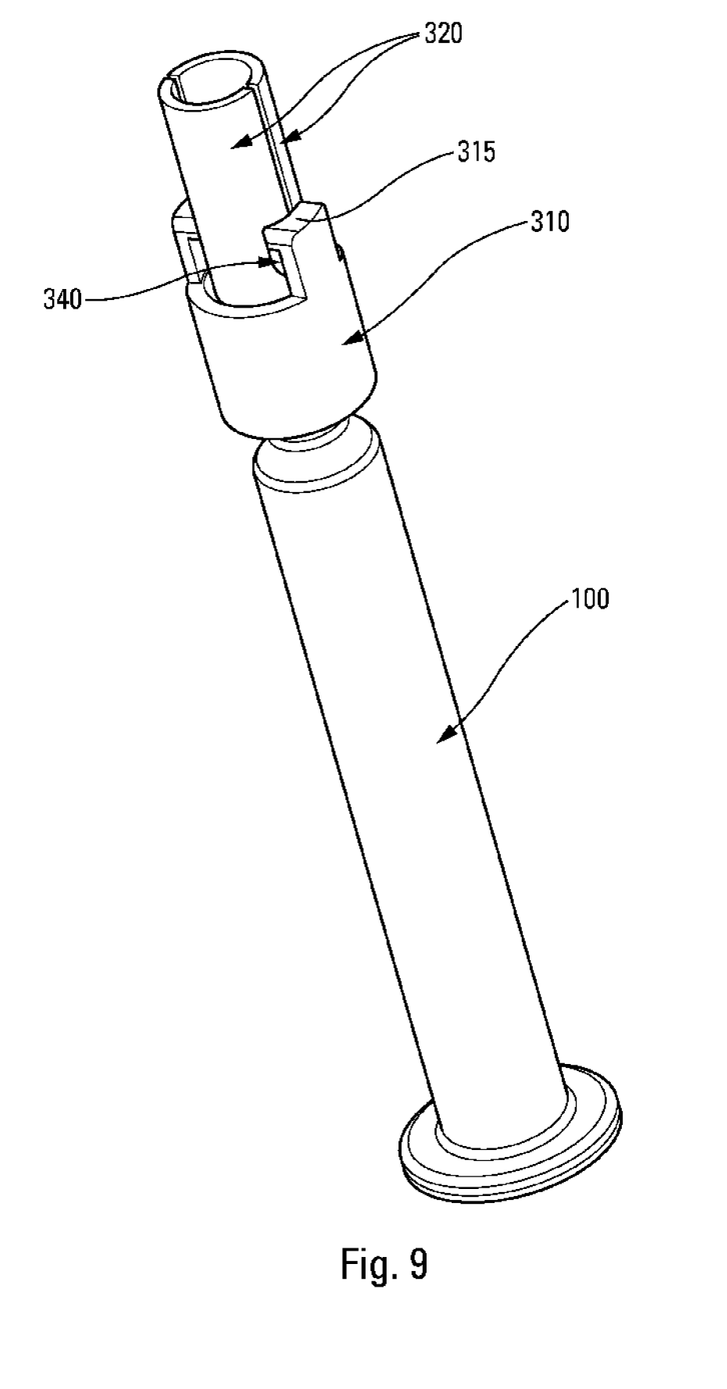
FIG. 9 is a view similar to that of FIGS. 6 and 7, in end of injection position.

FIGS. 3 to 5 show advantageous variant embodiments incorporating proof of initial usage.

In these variants, the outer body 220 comprises a protection part 229 which is connected to the fixing part 228 by at least one breakable material bridge 227. So, the outer body 220 is made of a single piece, and during withdrawal of the needle protection device, said at least one breakable material bridge 227 is broken, which forms proof of initial usage. For the needle protection device to be withdrawn, the breakable material bridge(s) has/have to be broken, and once broken it is no longer possible to return it to the initial state. The user who sees intact material bridges therefore knows that the needle protection device has not been removed. If on the contrary the material bridges are broken, he knows that there is the risk of loss of sealing and therefore contamination. Of course, the force necessary to disassemble the fixing part 228 of the injection device 100 must be greater than the force necessary to break the material bridge or bridges. Therefore, it is ensured that it is always the material bridges which will break first, and it will not be possible to remove the needle protection device without breaking said material bridges.

The fixing part 228 is fixed on the injection device, in particular clipped on the bowl of the syringe, as described previously. The protection part 229 is fixed to said inner body 210, in particular by wedging of the radial projection 215 of the inner body 210 between the radial shoulder 225 and the axial end edge folded back 226.

FIG. 3 shows a variant embodiment, in which the material bridges 227 are broken by axially pulling on the protection part 229. When there is sufficient force, the material bridges 227 break, and the protection part together with the inner body 210 can be withdrawn from the injection device 100, while the fixing part 228 remains fixed to the bowl of the syringe.

In FIG. 4, the material bridge(s) 227 are broken by pulling laterally on a tongue 230, which is fixed on one side to said fixing part 228 by at least one material bridge 227 and on the other side to said protection part 229 by at least one material bridge 227.

In FIG. 5, the protection part 229 of the outer body 220 comprises at least one manual deformation area 223, with rupture of the material bridge(s) 227 is achieved by clamping of said at least one manual deformation area 223. Advantageously, two manual deformation areas 223 are provided by being diametrically opposite each other, each of said areas 223 being connected to a material bridge 227 which breaks when the corresponding area is clamped or otherwise deformed manually.

FIGS. 6 to 9 illustrate another variant embodiment, in which the needle protection device 200 further comprises a protection system 300 against accidental pricking, in particular after use of the injection device 100.

In this variant, the protection system 300 comprises a control ring 310, preferably made of rigid plastic, as is the outer body 220 of the needle protection device 200. This control ring 310 is slidably mounted on said outer body 220.

The outer body 220 advantageously comes apart in two parts. A protection part 229 enabling withdrawal of the inner body 210, and a fixing part 228 which fixes on the injection device 100 and further comprises protective flaps 320. The protection part 229 is connected to the fixing part 228, in particular to said protective flaps 320, by breakable material bridges 227. The control ring 310 is slidably mounted about said fixing part 228.

The control ring 310 comprises at least one axial end edge part 315, preferably two, which cooperate(s) with said protective flaps 320 as will be described hereinbelow.

The protective flaps 320 are pivoting and connected to said fixing part 228 by flexible hinges. They comprise axial tabs 325, preferably having rounded ends which cooperate with said axial end edge parts 315 of the control ring 310. The protective flaps 325, in closed or covering position, define windows 340 seen in particular in FIG. 6.

To complete the injection, the patient or health personnel must break said material bridges 227, remove the protection part 229 together with the inner body 210, and slide the control ring 310 in a first position which opens the protective flaps 320, and effect the injection, the needle 110 being uncovered.

After injection, to reduce the risk of accidental pricking, the patient or health personnel will push the control ring 310 into a second position, which will cause covering of the needle 110 by the protective flaps 320.

The uncovering of the needle 110 is done in two steps. A first step consists of withdrawing the inner body 210 from the needle protector, the second step is opening the protective flaps 320.

The withdrawal of the inner body 210 is achieved by removal of the protection part 229 which is possible after breaking the breakable material bridges 227.

The protective flaps 320 are opened by sliding the control ring 310 towards the distribution orifice 111 of the needle 110. This ascent (in the position in FIGS. 6 to 9) provides thrust by the control ring 310 on the protective flaps 320, the axial end edge parts 315 of the control ring 310 pushing on the ends of the axial tabs 325 of the protective flaps 320. This thrust causes pivoting of the protective flaps 320 about their flexible hinges, uncovering the needle 110. After the injection, the needle 110 is secured by a second thrust of the control ring 310 towards the end of the needle which comprises the distribution orifice 111. This second thrust must therefore be sufficient to overcome said first blocking means.

This second thrust involves liberating the axial tabs 325, enabling said control ring 310 to push the protective flaps 320 to close them.

The windows 340 allow passage of the control ring 310, and in particular of the axial end edge parts 315, during covering of the needle 110 by closing of the protective flaps 320.

This position with the needle uncovered is advantageously held by first blocking means, for example a first groove 381 of the control ring 310 which cooperates with a first groove 281 of the fixing part 228.

This position is advantageously held by second blocking means, for example a second groove 382 of the control ring 310 and/or a second groove 282 of the fixing part 228.

Figure 10:
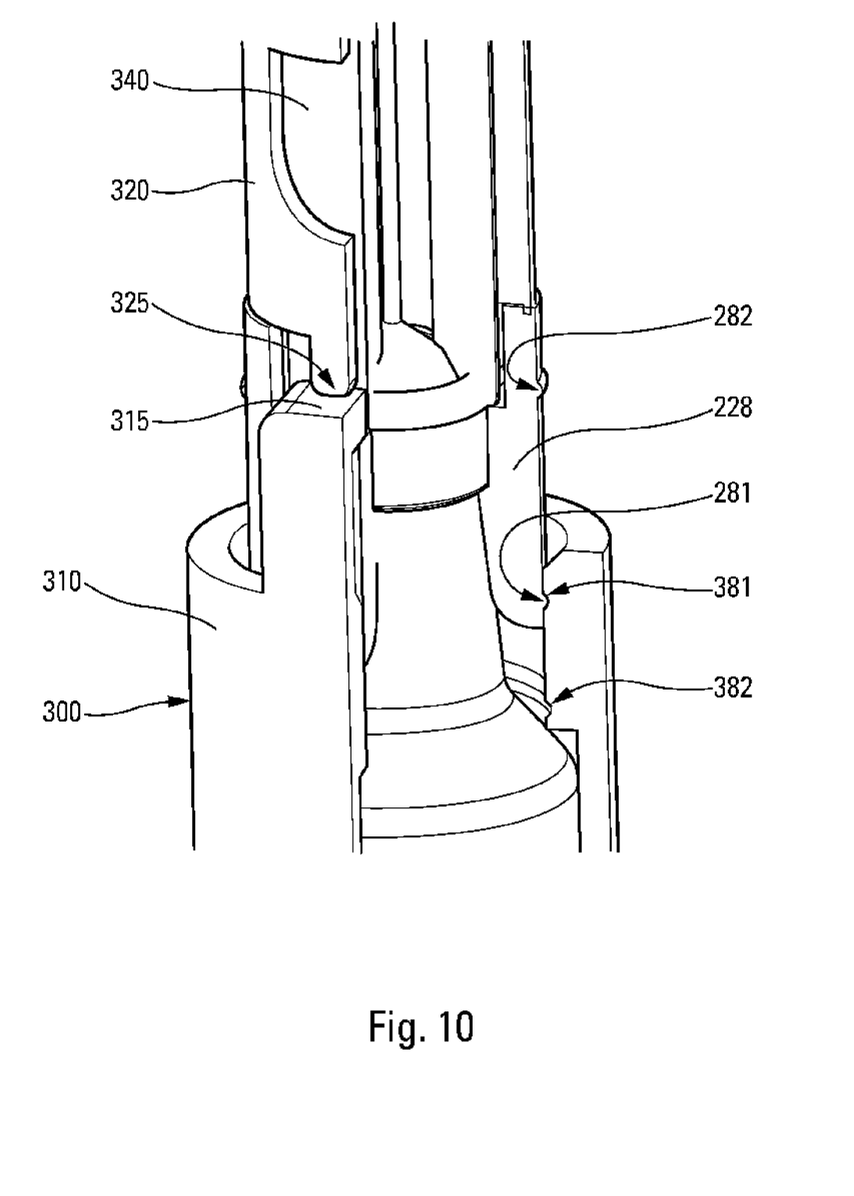
FIG. 10 is a schematic view in partially cut-away perspective, showing the device of FIGS. 6 to 9.

Blocking means of the control ring 310 relative to said outer body 220 are advantageously provided on said control ring and/or on said outer body, in particular its fixing part 228. These blocking means can be made in various ways. For example, as shown in FIG. 10, the control ring 310 can comprise two grooves 381, 382 offset axially, and the fixing part 228 of the outer body 220 can comprise two grooves 281, 282, also offset axially. Before actuation, the first groove 381 cooperates with the first groove 281. When the user wants to use the device, he pushes on the control ring 310 with sufficient force to overcome these blocking means and slide the control ring on said outer body 220, to open the protective flaps 320, as explained previously. In the open position of the flap sections, the second groove 382 of the control ring will cooperate with the first groove 381 of the outer body to keep the control ring in this position of use. After injection, to reclose the flap sections 320, the user must again exert sufficient force to overcome the blocking means, and guide the control ring 310 towards the covering position of the protective flaps, in which the first groove 381 of the control ring will cooperate with a second groove 282 of the outer body.

Of course, the blocking means can be made in different ways. So, a single groove of the control ring can cooperate with two or three grooves of the fixing part. As a variant, two or three grooves of the control ring could cooperate with a single groove of the fixing part. Optionally, two grooves and two grooves offset identically can be provided such that in the opening position of the flap sections there is double clipping of the two grooves on the two grooves.

Of course, these blocking means could also be reversed, with one or two grooves on the fixing part and one or two grooves on the control ring. Other configurations are also possible.

The example of FIGS. 6 to 9 combines a protection system 300 with proof of first usage, but it is quite possible to make the protection system 300 independently of proof of first usage.

Of course, the invention is not limited to the embodiments illustrated in the drawings, and by contrast the scope of the invention is defined by the appended claims.

The invention claimed is:

1. An injection device for a fluid product comprising a syringe body that is an integral one-piece construction and a needle fixed in an axial end projection of the syringe body, said axial end projection being defined between an axial end surface of the syringe body and a radial projection, said injection device comprising a needle protection device, said protection device being, in a storage position, fixed to the syringe body, said protection device being removable from said syringe body, said protection device comprising an inner body made of substantially supple or deformable material and an outer body made of substantially rigid material, said inner body comprising a proximal axial end edge, said inner body, in a storage position, sealingly closing the distribution orifice of said needle with an axial end of said needle being embedded in said inner body, and said inner body sealingly cooperating with said syringe body, said sealing with the syringe body being achieved by contact between said axial end surface of the syringe body and said proximal axial end edge of said inner body, and said outer body in a storage position, cooperating with said syringe body to fix said protection device on said syringe body, wherein said outer body comprises a fixing part fixed to said radial projection of said axial end projection, and a protection part fixed to said inner body, said protection part being connected to said fixing part by at least one breakable material bridge, said at least one breakable material bridge being broken to remove said protection part and said inner body from said syringe body.

2. The device according to claim 1, wherein a force necessary to remove said fixing part from the syringe body is greater than the force necessary to break said at least one breakable material bridge.

3. The device according to claim 1, wherein a tongue is interposed between said fixing part and said protection part, said tongue being connected to said fixing part by at least one breakable material bridge and being connected to said protection part by at least one breakable material bridge.

4. The device according to claim 1, wherein said protection part of the outer body comprises at least one manual deformation area, the rupture of the material bridge(s) is achieved by clamping of said at least one manual deformation area.

5. The device according to claim 1, wherein said inner body comprises a radial projection and said outer body comprises a radial shoulder and an axial end edge defining an upper axial opening, said inner body being inserted into said outer body with said radial projection stopped on said radial shoulder, said axial end edge of said outer body being folded back on said inner body to fix said inner body in said outer body.

6. The device according to claim 1, comprising a protection system against accidental pricking.

7. The device according to claim 1, wherein said inner body is made of rubber.

8. The device according to claim 1, wherein the fixing part is clipped on to said radial projection of said axial end projection.

9. The device according to claim 1, wherein said inner body made of substantially supple or deformable material that sealingly closes the distribution orifice of said needle is a one-piece integral construction that comprises said proximal axial end edge of said inner body that sealingly cooperates with said syringe body and is in direct contact with said syringe body.

10. The device according to claim 4, wherein two diametrically opposite manual deformation areas (223) are provided, each of said manual deformation areas (223) being connected to at least one material bridge (227) which breaks when said corresponding manual deformation area is deformed manually.

11. The device according to claim 5, wherein said axial end edge of said outer body is folded back on said inner body before assembly of said needle protection device on said syringe body.

12. The device according to claim 6, wherein said protection system comprises protective flaps forming an integral part of said outer body, said protective flaps being movable between a covering position, in which they cover the needle and an open position, in which the needle is uncovered, said protection system further comprising a control ring sliding on said outer body to, before injection, move said protective flaps from their covering position towards their open position, then after injection, from their open position towards their covering position.

* * * * *